United States Patent [19]

Duffy et al.

[11] Patent Number: 5,612,047
[45] Date of Patent: Mar. 18, 1997

[54] PESTICIDAL MICROEMULSION FORMULATION

[76] Inventors: Eric P. Duffy, 13561 Rawhide Pkwy., Farmers Branch, Tex. 75234; Joe D. McDaniel, Jr., 1112 Alameda, Carrollton, Tex. 75007; William A. Donahue, 2307 Harbinger La., Dallas, Tex. 75287

[21] Appl. No.: 207,862

[22] Filed: Mar. 8, 1994

[51] Int. Cl.$^6$ .................................... A01N 25/16
[52] U.S. Cl. .................... 424/405; 424/403; 424/484; 424/DIG. 3; 424/DIG. 8; 424/DIG. 10; 514/919; 514/937; 514/944; 514/945
[58] Field of Search .................... 424/484, 405, 424/403, DIG. 10, DIG. 8; 514/944, 937, 919, 945

[56] References Cited

U.S. PATENT DOCUMENTS

| | | | |
|---|---|---|---|
| 3,159,535 | 12/1964 | Sesso et al. | 424/405 |
| 3,683,078 | 8/1972 | Haus | 424/484 |
| 3,954,967 | 5/1976 | Urton | 424/DIG. 10 |
| 4,851,438 | 7/1989 | Flashinski et al. | 424/405 |

FOREIGN PATENT DOCUMENTS 282706  9/1988  European Pat. Off. .
516590  2/1992  European Pat. Off. .

OTHER PUBLICATIONS

Comstock, M. J. (1985). Bioregulators for pest control. ACS, pp. 200–218.

CA 103:2100 (1985).

*Primary Examiner*—Raj Bawa
*Attorney, Agent, or Firm*—Lynn Marcus-Wyner

[57] ABSTRACT

This invention relates to a stable pesticidal microemulsion formulation comprising from about 0.01 to about 25% by weight of an insect growth regulator, for example methoprene, S-methoprene, hydroprene and/or S-hydroprene, and from about 0.1 to about 5.0% by weight of an active ingredient, for example pyrethroids or permethrins, and from about 3 to 50% by weight of one or more surfactants with a hydrophile-lipophile balance value of 6 or higher, and from about 25 to 98% by weight of water wherein the insect growth regulator and active ingredient are dispersed in the surfactant(s) forming an oil phase which is in turn dispersed in water and forms discrete micelles in the range of about 0.001 to about 0.5 micrometers. This invention also teaches a method of applying the stable pesticidal microemulsion on animals to control ticks and fleas.

11 Claims, No Drawings

5,612,047

PESTICIDAL MICROEMULSION FORMULATION

BACKGROUND AND SUMMARY OF THE INVENTION

This invention concerns novel pesticidal emulsions capable of being formed as stable microemulsions which may be shipped and reconstituted for application.

Pesticidal microemulsion formulations are defined as transparent thermodynamically stable dispersions of two or more immiscible liquids in each other containing varying amounts of surfactants. These formulations are classified as water-in-oil (w/o) or oil-in-water (o/w) and generally include four basic components, water, oil, surfactant and alcohol. The present invention relates to oil-in-water formulations wherein the dispersed phase, the oil phase, consists of small droplets of minces of the active ingredient surrounded by surfactant and held in a continuous aqueous phase. Pesticidal microemulsions are known in the art and U.S. Pat. Nos. 3,954,967 and 3,683,078 are illustrative of such formulations.

In general, microemulsions are produced with a large percentage of surfactant and solvent in the oil phase. The surfactant is required to cover the large surface area comprising the dispersed oil phase.

One serious problem encountered with microemulsions is the "settling out" of the emulsified material which then results in turbidity giving rise to uneven activity and general lack of acceptability. Therefore, maintenance of stability with good efficacy in the presence of an emulsifier is an important criterion for an effective and acceptable microemulsion.

It has now been found that stable pesticidal microemulsions are readily obtained by careful control of micelle size. More particularly, the formulation of this invention is a stable pesticidal microemulsion comprising a) from about 0.01 to about 25% by weight of an insect growth regulator;

b) from about 3 to about 50% by weight of one or more surfactants;

c) from about 25 to about 98% by weight of water wherein component a) is dissolved in component b) to yield an oil phase which is dispersed in component c) and said dispersed off phase forms discrete micelles in the range of about 0.001 to about 0.50 micrometers.

Illustrative of a preferred process according to the invention is a process for preparing a stable microemulsion comprising a) forming an initial oil phase comprising one or more pesticidally effective compounds and one or more surfactants; b) forming a separate aqueous phase comprising the mixture of water, chelating agents and buffers; and c) adding the aqueous phase to the oil phase until homogeneous wherein the oil phase is dispersed in the aqueous phase to form minces in the range of about 0.001 to about 0.50 micrometers.

A preferred embodiment of the present invention comprises a microemulsion formulation wherein the active ingredient includes methoprene, typically in the range from about 0.05 to about 25%. Additionally, formulations may comprise more than one active ingredients, for example methoprene and synergized pyrethrins.

It is envisaged that the microemulsion of the present invention will be used as typical for pest control but especially for control of fleas and ticks on domestic animals such as dogs and cats as a dip concentrate.

Typically and particularly with respect to dip concentrates active ingredients are formulated as emulsifiable concentrates, wherein the active ingredient is dissolved in a hydrocarbon solvent. Frequently the end user adds oil to the water phase and forms a macroemulsion. Therefore, another embodiment of the invention is a microemulsion wherein the active ingredient(s) is dissolved in one or more surfactants without a solvent and wherein water forms the continuous aqueous phase that contains the discrete micelles. Accordingly the preferred active ingredient is methoprene.

When methoprene is the active ingredient it has been found that an alkylated hydroxy benzene should be included in the oil phase to increase the stability of the methoprene. Accordingly, in a preferred embodiment the percent range on a weight basis of each component is about 0.05 to about 15 of active ingredient; 3 to about 50 of surfactant; 0.1 to about 2.0 of an alkylated hydroxy benzene; about 0.01 to about 0.5 of a chelating agent; about 0.01 to about 0.5 of a buffering agent and about 30 to about 65 water.

DETAILED DESCRIPTION OF THE INVENTION

The microemulsions according to the invention are particularly useful when the active ingredient is a pesticide such as a herbicide, plant growth regulator, fungicide or especially an insecticide. Combinations of one or more of each of such pesticides may be also employed. The choice of active ingredient(s) is not usually critical, but the active ingredient must be soluble in at least one component of the system.

The microemulsions according to the invention are particularly suitable in formulating insect growth regulators (IGRs) including juvenile hormones, juvenoids and chitin synthesis inhibitors. Examples of IGRs include the juvenoids methoprene, hydroprene, kinoprene. These active ingredients bear an asymmetric carbon atom and, accordingly, there are (R) and (S) enantiomers of these compounds. As used herein "(R,S)" refers to the racemic mixture and "(S)" refers to the compound comprising a predominance of the (S)-(+) enantiomer. Where the compound name is used herein without reference to its enantiomeric content, the term is inclusive of both (R,S) and (S) forms.

Examples of active ingredients which may also be suitable for use in the practice of the invention include 2-chloro-N-[[[3.5-dichloro-4-[3,4,5-trichloro- 1-pyrazolyl]phenyl]amino]carbonyl]-benzamide, (cf US Pat. No. 4,950,678 the contents of which are incorporated herein by reference) propetamphos, fluvalinate, fluphenacur, cyromazine, chlorfluazuron, fenoxycarb, diflubenzuron, flucycloxuron, hexaflumuron, teflubenzuron, flufenoxuron, triflumuron, pyriproxyfen, chlorpyrifos ethyl, chlorpyrifos methyl, cypermethrin, lambda-cyhalothrin, cyfluthrin, fenvalerate, esfenvalerate, deltamethrin, fenpropathrin, bifenthrin, permethrin, ethofenprox, tralomethrin, alphacypermethrin, bendiocarb, RH 5849 (Rohm & Haas), flucycloxuron, flucythrinate, pyrethrins, allethrin, prallethrin, furethrin, acrinathrin, cyhalothrin, cyphenothrin, phenothrin, resmethrin, tefluthrin, tetramethrin, dimethrin, fenfluthrin, flumethrin, pyresmethrin, terallethrin, tralocythrin, cyclopro-thrin, synergized pyrethrin and the like.

The amount of active ingredient required in the microemulsion formulations will depend on various factors such as efficacy, solubility in the system, intended use and the like and may be readily determined by one skilled in the an by routine experimentation. For example, when employing a juvenoid such as methoprene the amount of active ingredient present is preferably from about 0.05 to about 15% w/w. In a preferred embodiment a stable pesticidal microemulsion formulation of the invention comprises a dispersed oil phase including from about 0.05 to about 5.0% by weight of (S) methoprene; from about 1.0 to about 5.0% by weight of pyrethrin; from about 1.0 to about 15.0% by weight of pyrethrin synergist; from about 0.01 to about 2.0% by weight of a butylated hydroxy toluene; and from about 15 to 30% of one or more surfactants; and a continuous aqueous phase including from about 30 to about 60% by weight of water wherein the dispersed phase consists of micelles in the range from about 0.001 to about 0.50 micrometers.

By the term surfactant it is understood that wetting agents, dispersing agents, suspending agents and emulsifiers are included therein. Anionic, nonionic and amphoteric agents and mixtures thereof can be used with equal facility.

Examples of suitable surfactants include alkylbenzene sulfonates, alpha-olefin sulfonates, sulfosuccinates, alcohol ether sulfates, nonylphenol ethoxylate sulfates, phosphate esters, linear alkyl ethoxylates, alkylaryl ethoxylates, polyethylene glycol esters, ethoxylated vegetable oil, ethoxylated castor oil, polyoxyethylene/polyoxypropylene block polymers, ethoxylated triglycerides (non-ionic) ethoxylated fatty acids (non-ionic). Such surfactants preferably have an HLB of approximately 12. The HLB (hydrophile-lipophile balance) is an expression of the relative simultaneous attraction of an emulsifier (or surfactant) for water and oil. It is determined by the chemical composition of a given surfactant. Surfactants or emulsifiers with low HLB values and in particular less than 6 tend to make water-in-oil emulsions. The HLB values of many surfactants can be obtained from publications for example, McCutcheon's volume 1:Emulsifiers and Detergents, 1993, North American Edition.

In addition to the suitable nonionic surfactants, anionic surfactants are particularly preferred when non-polar active compounds are incorporated into the microemulsion. The preferred range for anionic surfactants is from about 0.1 to about 5% by weight and more preferably from about 0.3 to about 3.0% by weight. In general the range of surfactants can be from about 3.0 to 50% by weight and more preferably from about 15% to about 25% by weight.

Specific examples of emulsifying agents include anionic co-surfactants, nonionic blends, amphoteric and hydrotropic agents such as calcium alkylbenzene sulfonate, phosphate esters, block polymers, and ethoxylates. As one in the art is aware emulsifying agents are a type of surface active agent which stabilizes a suspension of droplets of one liquid in another liquid. Some emulsifiers are known to be incompatible for example anionic and cationic emulsifier are generally not used together because one precipitates the other. However, either cation or anion emulsifiers may be used with nonionic or amphoteric agents.

The following surfactants have been found to be useful in the process and formulations of this invention.

| Surfactant | Manufacturer | Structure/Type |
| --- | --- | --- |
| Alfonic | Vista Chemical | ethoxylated alcohol |
| PEG-30 | STEPAN | polyethylene glycol |
| Tween | ICI Americas | polyoxyethylene fatty ester |
| Pluronic F | BASF | block copolymer |
| Micro-Step H303 | STEPAN | nonionic blend |
| Toximul 8241 | STEPAN | castor oil ethoxylate |
| Mapeg Co 30 | PPG Industries | nonionic blend |
| SPONTO Seris | Witco | blend polyoxyehtylene |

| Surfactant | Manufacturer | Structure/Type |
| --- | --- | --- |
| ETOCAS 30 | Croda | polyehtylene glycol |
| Ethox M | Ethox Chemicals | ethoxylated fatty acid |
| AL 1447 | ICI Americas | ethoxylated triglyceride |

The microemulsion formulation may also include alkylated hydroxy benzenes which are antioxidants and food acceptable non-flammable, mono- or poly-alkylated phenols, cresols or xylenols such as 4-sec-butylphenol; 4-ethylphenol; 2-methyl-6-ethylphenol; 3-methyl-4-tert-butylphenol;2,4-dimethyl-6-tert-butylphenol;4-methyl-2-tert-butylphenol and 4-methyl-2,6-di-tert-butylphenol. Especially preferred is 4-methyl-2-di-tert-butylphenol also referred to as 2,6-di-tert-butyl-4-cresol, or butylated hydroxy toluene (hereinafter BHT).

In addition to active ingredient(s), surfactants and alkylated hydroxybenzenes the microemulsions may contain other substances such as solvents, buffers, chelating agents, fragrances and other additives common in the preparation of microemulsions.

Examples of solvents include saturated aliphatic hydrocarbons, (parifinic, naphthenic), water, long chain alcohols, e.g. Linalool®, aromatic hydrocarbons (TENNECO 500-100®), lactones, e.g. N-methyl-2-pyrrolidone and esters.

Examples of buffers include monobasic potassium phosphate, potassium sorbate, citric acid, sodium hydroxide and other G.R.A.S. buffers.

For use on animals a pH of about 7.0 is preferred. For crop uses a more acid or basic formulation may be required to preserve the active ingredient.

Examples of chelating agents include tetrasodium EDTA, e.g. Sequestrene® 30A or 220, pentasodium salt of diethylene-triamine penta acetic acid, e.g. Chel DTPA 41® (Ciba-Geigy).

Examples of other additives include silicone oils e.g. dimethylsiloxane polymers (e.g. Dow Coming fluid), dimethicone copolyol, cyclomethicone, dimethicone, phenyldimethicone, trimethylsiloxysiliate, and polyalkylene oxide modified methyl polysiloxanes, e.g. Silwet® (Union Carbide).

Fragrances, repellents, attractants, pigments and other customized additives may also be employed depending on the particular use. These are well known in the art.

Such additives may include an anionic sulfosuccinate of higher fatty acid monoethanolamide as a skin antiirritant for animal products; an amphoteric sulfonated fatty amide for use in carpet shampoos; and a substituted carboxylated cocoimidazoline organophosphate hydrotrope as a synergistic with non-ionic surfactants as a wetting agent.

The microemulsions are prepared by mixing of the non-aqueous ingredients followed by addition with moderate stirring of the aqueous phase.

Many of the surfactants in the instant formulations will spontaneously over a period of time, form microemulsions. However, in some cases, for example, MICROSTEPH 303, it is preferred to warm the formulation to the surfactants cloud point and then allow it to cool to room temperature. A transparent gel or at high water concentrations a microemulsion will be produced without shear. Certain surfactants, for example polyethylene glycol castor oil, require shear.

In accordance with the invention, the oil phase forms micelles or droplets wherein the active ingredient(s) is surrounded by surfactant and held in the continuous phase.

The term "micell" or droplet includes micells, particles, droplets and the conical, hexagonal or lamella shaped structures formed by the dispersed oil phase. The size of the micells is from about 0.001 to about 0.5 micrometers, preferably about 90% of the micells will range in size from about 0.001 to 0.2 micrometers.

The size of the micells in the present invention is particularly important. It is suggested that the small size of the micell imparts stability to the microemulsion and further provides superior efficacy relative to macroemulsion formulations having the same level of active ingredient. Formulations with micells greater than 0.5 micrometers may appear turbid.

Micell size can be determined readily by low angle x-ray, neutron capture, electron microscope, membrane osmentry or magnetic nuclear resonance diffusion. In a microemulsion, light is allowed to pass through the formulation unhindered or at most slightly refracted. Microemulsions generally exhibit high birefringence to polarized light.

The stability and efficacy of the microemulsions according to the present invention which have sub-micron particle size is such that they can be formulated as stable concentrates for transportation which may be reconstituted for end use with water either as a finished product or as an addition to a water based formulation, e.g. as a tank mix for agricultural use or as a carpet shampoo. For example for animal use they may be reconstituted as dips, sprays, pour-ons, spot-ons, conditioning creams, aerosol mouses and the like.

The following examples are provided to illustrate specific embodiments of the invention. As will be recognized by one skilled in the art, these examples are illustrative and are not meant to be limiting. Temperature is given in degrees Celsius. Percentages are given as percent by weight.

EXAMPLE 1

|   |   | Microemulsion Formulation | |
|---|---|---|---|
|   |   | % w/w | gms/batch* |
| A. | (S)-Methoprene | 3.6 | 14.4 |
| B. | BHT | 0.50 | 2.0 |
| C. | Pyrethrum 175 | 9.5 | 38.0 |
| D. | PBO | 4.8 | 19.2 |
| E. | MGK 264 | 5.9 | 23.6 |
| F. | Linalool | 1.00 | 4.0 |
| G. | PEG-40 Castor Oil | 23.00 | 92.0 |
| H. | KH$_2$PO$_4$ | 0.20 | 0.8 |
| I. | NaEDTA | 0.20 | 0.8 |
| J | H$_2$O | 51.3 | 205.2 |

A = isoproyl (2E, 4E, 7S)-11-methoxy-3,7,11-trimethyldodeca-2,4-dienoate (90% a.i.) (cf U.S. Pat. No. 3,904,662) the contents of which are incorporated herein by reference).
B = 2,6-di-tert-butyl-4-cresol.
C = 20% pyrethrin dissolved in isoparaffinic hydrocarbon solvent (mineral oil) 80%
D = Piperonyl butoxide, (2-(2-butoxyethoxy)ethyl-6-propylpiperonyl ether).
E = N-octyl bicycloheptene dicarboximide (N-(2-ethylhexyl)-8,9,10-trinorborn-5-ene-2,3-dicarboximide 98% a.i.
F = 3,7-Dimethyl-1,6-octadien-3-ol.
G = Polyethylene glycol derivative of castor oil with an average of 40 moles of ethylene oxide.
*a batch is 400 grams Ingredients A through G comprise the oil phase and are mixed together in a vessel by adding the ingredients in order with moderate stirring. The vessel can be placed in hot tap water to effect solution of the BHT. The active ingredients are dissolved in the surfactant without additional solvent. Ingredients H, I, J comprise the water phase and are mixed in the same manner in a separate vessel. With robust, high-shear mixing the water phase is slowly added to the oil phase to produce the desired microemulsion.

EXAMPLE 2

|   |   | % w/w | gms/batch |
|---|---|---|---|
| A. | (S) Methoprene | 0.08 | 0.8 |
| B. | BHT | 0.10 | 1.0 |
| C. | Pyrethrum 175 | 0.50 | 5.0 |
| D. | PBO | 0.35 | 3.5 |
| E. | MGK 264 | 0.60 | 6.0 |
| F. | Linalool | 0.50 | 5.0 |
| G. | Microstep 303 | 5.00 | 50.0 |
| H. | NaEDTA | 0.10 | 1.0 |
| I. | KH$_2$PO$_4$ | 0.10 | 1.0 |
| J. | H$_2$O | 92.67 | 926.7 |

The ingredients of the formulation are as described hereinabove in Example 1. Microstep 303 is a proprietary nonionic blend surfactant of STEPAN Company.

EXAMPLE 3

|   |   | % w/w | gms/batch |
|---|---|---|---|
| A. | (S) Hydroprene (90%) | 14.1 | 49.4 |
| B. | BHT | 0.5 | 1.8 |
| C. | Permethrin 175 | 10.9 | 38.2 |
| D. | Linalool | 1.0 | 3.5 |
| E. | Microstep 303 | 30.0 | 105.0 |
| F. | KH$_2$PO$_4$ | 0.2 | 0.7 |
| G. | NaEDTA | 0.2 | 0.7 |
| H. | H$_2$O | 43.0 | 150 |

The ingredients of the formulation are described hereinabove in Examples 1 and 2.
A = (S) Hydroprene is ethyl (2E, 4E)-3,7,11-trimethyldodeca-2,4-dienoate.

STABILITY STUDIES

A. The following 400 gram formulation was tested for stability.

|   | Ingedient | % w/w | gms/batch |
|---|---|---|---|
| A. | S-methoprene | 6.0 | 24 |
| B. | BHT | 0.2 | 0.8 |
| C. | PEG-25 Castor Oil | 12.0 | 48.0 |
| D. | Potassium phosphate | 0.8 | 3.2 |
| E. | Sodium hydroxide (30% aqueous) | 0.3 | 1.2 |
| F. | Potassium sorbate | 0.2 | 0.8 |
| G. | H$_2$O | 80.5 | 322.0 |
|   |   | 100 | 400.0 |

C = Polyethylene glycol derivative of castor oil with an average of 25 moles of ethylene oxide.
E = Alkalizer.
F = Mold and yeast inhibitor.

The other ingredients of the formulation are as described hereinabove.

The components of the oil phase, methoprene, BHT and PEG-25 Castor oil are mixed together in a beaker placed in hot tap water to effect solution of the BHT. The components of the water phase are mixed and slowly added to the oil phase. The solution is stirred until homogenous and packaged in four clear glass bottles. The appearance of the product is clear to very slightly turbid yellowish.

One sample is maintained at room temperature as a control sample. Eleven and 26 days after formulation the control sample remains unchanged, there is no observable separation.

A 4 oz. sample is placed in a 50°–54° C. oven, and observed 11 and 26 days after storage. There is no observable separation of the emulsion. At 11 days the oven sample is cooled to room temperature and it reverts to a clear yellowish microemulsion. The sample is returned immediately to the 50° C. oven.

A 4 oz. sample is placed in a freezer for freeze-thaw stability. After 26 days the sample has been through 5 cycles in the freezer. The sample remains homogenous after one inversion.

B. Physical stability of S-methoprene formulations placed in an oven at 54° C.

|  | Ingredient | Formulation % w/w | | | |
|---|---|---|---|---|---|
|  |  | 1 | 2 | 3 | 4 |
| A = | S-Methoprene | 5.0 | 6.0 | 6.0 | 5.0 |
| B = | Emulphor EL-620 | 10.0 | 12.0 | 10.0 | — |
| C = | Mapeg Co. 25 | — | — | — | 10.0 |
| D = | D.I. H$_2$O | 68.3 | 82.0 | 84.0 | 68.3 |
|  | Total (gms) | 83.3 | 100.0 | 100.0 | 83.3 |

Formulations were prepared as described hereinabove. After four weeks of storage, formulation 1,2 and 3 were unchanged, still clear with no separation, one phase. Formulation 4 did develop an opaque, flocculant precipitate floating in the top of the container.

B=ethoxylated vegetable oil.

C=PEG-25 castor oil.

EFFICACY STUDIES

A formulation containing 1.93% Pyrethrin, 3.84% PBO, 5.76% MGK-264 and 3.24% S-methoprene was evaluated for ovicidal and insecticidal activity against *Ctenocephalides feles* (Bouché) (hereinafter *C. felis*) with adult flea infestations on cats. The above formulation gave a ratio of 1:2:3:1.7. This formulation was diluted with water at a rate of 2 oz per gallon to give a final dip solution of 0.03% Pyrethrin, 0.06% PBO, 0.09% MGK-264 and 0.05% S-methoprene.

On day 0 each cat is dipped into the solution. A placebo formulation without active ingredients is also prepared as a dip solution. On days 2, 3, 7, 10, 14, 17, 21 and weekly thereafter through day 98 cats are infested with approximately 100 unfed adult fleas (*C. felis*). On days −1, 0+2 hr, 0+4 hr, 1, 2, 3, 7, 10, 14, 71, 21 cats are combined to evaluate their flea infestation.

The % flea control efficacy provided by the dip treatments as compared to the controls is calculated using Abbotts formula (J. Econ. Entomol., 18 pp 265–267, 1925) and the results are presented in Table 1 below.

TABLE 1

| Time After Treatment | % Flea Control |
|---|---|
| 0 + 2 hours | 67 |
| 0 + 4 hours | 95 |
| 1 day | 100 |
| 3 days | 96 |
| 7 days | 85 |
| 10 days | 85 |
| 14 days | 73 |
| 17 days | 57 |

A similar study was conducted on dogs to evaluate the efficacy of the formulation against *C. felis* and adult brown dog ticks (*Rhipicephalus sanguineus*). The test dip provided 94% mortality of adult cat fleas by 2 hours post dipping, 99–100% mortality through day 10, and 81% mortality at day 14. Treatment provided 100% mortality from day 1 through day 10 of adult *R.sanguineus*. By day 14 adult tick mortality declined to 72%. The ovicidal evaluations against *C.felis* began on day 25 giving 100% inhibition of ecolosion and generally maintained a level of greater than 90% inhibition of flea eggs hatching for 151 days.

What is claimed is:

1. A stable pesticidal microemulsion formulation comprising a dispersed oil phase including from about 0.05 to about 5.0% by weight of (S) methoprene; from about 1.0 to about 5.0% by weight of pyrethrins; from about 1.0 to about 15.0% by weight of pyrethrin synergists; from about 0.01 to about 2.0% by weight of a butylated hydroxy toluene; and from about 15 to 30% of one or more surfactants; and a continuous aqueous phase including from about 30 to about 60% by weight of water wherein the dispersed phase consists of micelles in the range from about 0.001 to about 0.50 micrometers.

2. The formulation of claim 1 further comprising chelating agents and buffering agents.

3. The microemulsion of claim 1 wherein the formulation is reconstituted for end use with water.

4. A method of controlling fleas and ticks on domestic animals comprising applying the pesticidal microemulsion of claim 1 to said animal.

5. A pesticidal microemulsion formulation comprising:
    (a) from about 0.01 to about 25% by weight of an insect growth regulator selected from the group methoprene, (S)-methoprene, hydroprene and (S)-hydroprene;
    (b) from about 0.1 to about 5.0% by weight of pyrethrin or synthetic pyrethoid;
    (c) from about 0.01 to about 5.0% by weight of an alkylated hydrobenzene;
    (d) from about 3.0 to about 50% by weight of one or more surfactants wherein said the hydrophile-lipophile balance value of the surfactant is not less than 6; and
    (e) from about 25 to about 98% by weight of water wherein components (a), (b) and (c) are dispersed in component (d) to yield an oil phase which is dispersed in component (e) and said dispersed off phase forms discrete micelles in the range of about 0.00 1 to about 0.50 micrometers.

6. The microemulsion of claim 5 wherein the alkylated hydroxybenzene is butylated hydroxytoluene.

7. The formulation of claim 5 further comprising buffering agents and chelating agents.

8. The microemulsion of claim 5 wherein the surfactant has an HLB of approximately 12.

9. The formulation of claim 5 wherein the formulation is reconstituted for end use with water.

10. A method of controlling fleas and ticks on domestic animals comprising applying the pesticidal microemulsion of claim 5 to said animal.

11. The method of claim 10 wherein the microemulsion is reconstituted as a dip, spray, pour-on, spot-on, conditioning cream, or aerosol mouse.

* * * * *